United States Patent
Boese et al.

(10) Patent No.: US 8,428,221 B2
(45) Date of Patent: Apr. 23, 2013

(54) MEDICAL X-RAY ACQUISITION SYSTEM

(75) Inventors: Jan Boese, Eckental (DE); Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 232 days.

(21) Appl. No.: 12/893,189

(22) Filed: Sep. 29, 2010

(65) Prior Publication Data
US 2011/0075814 A1 Mar. 31, 2011

(30) Foreign Application Priority Data
Sep. 29, 2009 (DE) .......................... 10 2009 043 424

(51) Int. Cl.
*H01J 35/06* (2006.01)
*H05G 1/02* (2006.01)
(52) U.S. Cl.
USPC ............................ 378/122; 378/193; 378/197
(58) Field of Classification Search .................. 378/119, 378/122, 193, 197
See application file for complete search history.

(56) References Cited

U.S. PATENT DOCUMENTS

| 4,326,144 | A | 4/1982 | Appelt |
| 4,609,940 | A | 9/1986 | Born et al. |
| 4,924,485 | A | 5/1990 | Hoeberling |
| 6,553,096 | B1 | 4/2003 | Zhou et al. |
| 7,359,484 | B2 | 4/2008 | Qiu et al. |
| 7,567,647 | B1 * | 7/2009 | Maltz .............................. 378/21 |
| 7,724,870 | B2 * | 5/2010 | Maltz et al. .................... 378/65 |
| 2004/0066906 | A1 | 4/2004 | Hornegger et al. |
| 2006/0002515 | A1 | 1/2006 | Huber et al. |
| 2008/0240363 | A1 | 10/2008 | Grebner et al. |
| 2008/0253516 | A1 * | 10/2008 | Hui et al. ........................ 378/62 |
| 2009/0060137 | A1 | 3/2009 | Fritzler et al. |

FOREIGN PATENT DOCUMENTS

DE 102005052131 A1 5/2007

OTHER PUBLICATIONS

"Xintek, Inc. Nanotechnology Innovations" (2009).
"XinRay System—Products and Technology" (2009).
"Nanotubes Sharpen X-ray Vision," Merali, Nature News (2009).

* cited by examiner

*Primary Examiner* — Irakli Kiknadze
(74) *Attorney, Agent, or Firm* — Schiff Hardin LLP

(57) ABSTRACT

A medical x-ray acquisition system has an x-ray source and an x-ray detector, the x-ray source having at least one field emission radiator with at least one field emission cathode. The field emission cathode can be formed by a nanostructured material with carbon nanotubes.

9 Claims, 3 Drawing Sheets

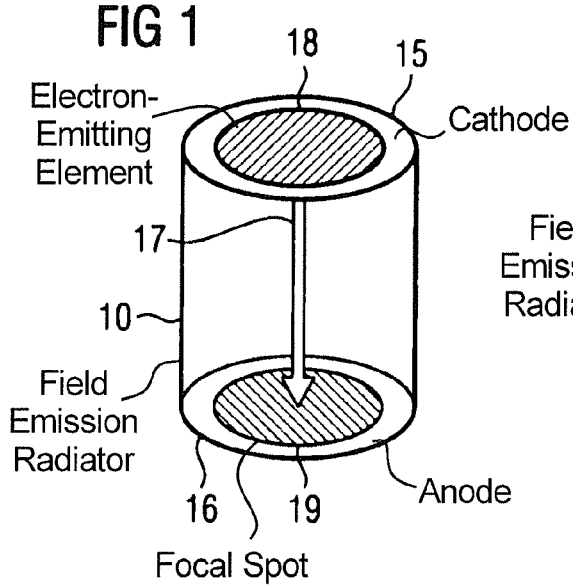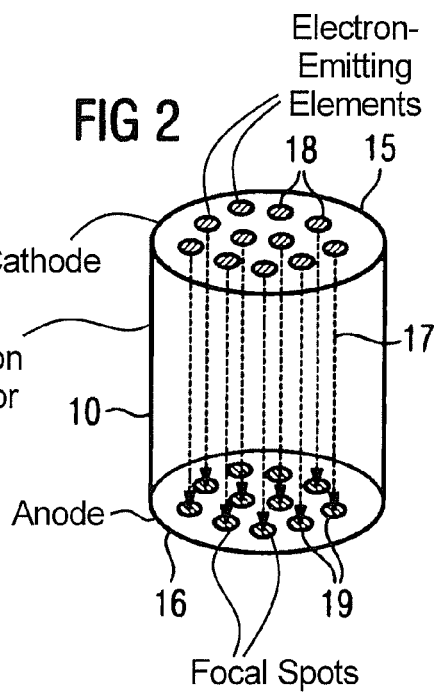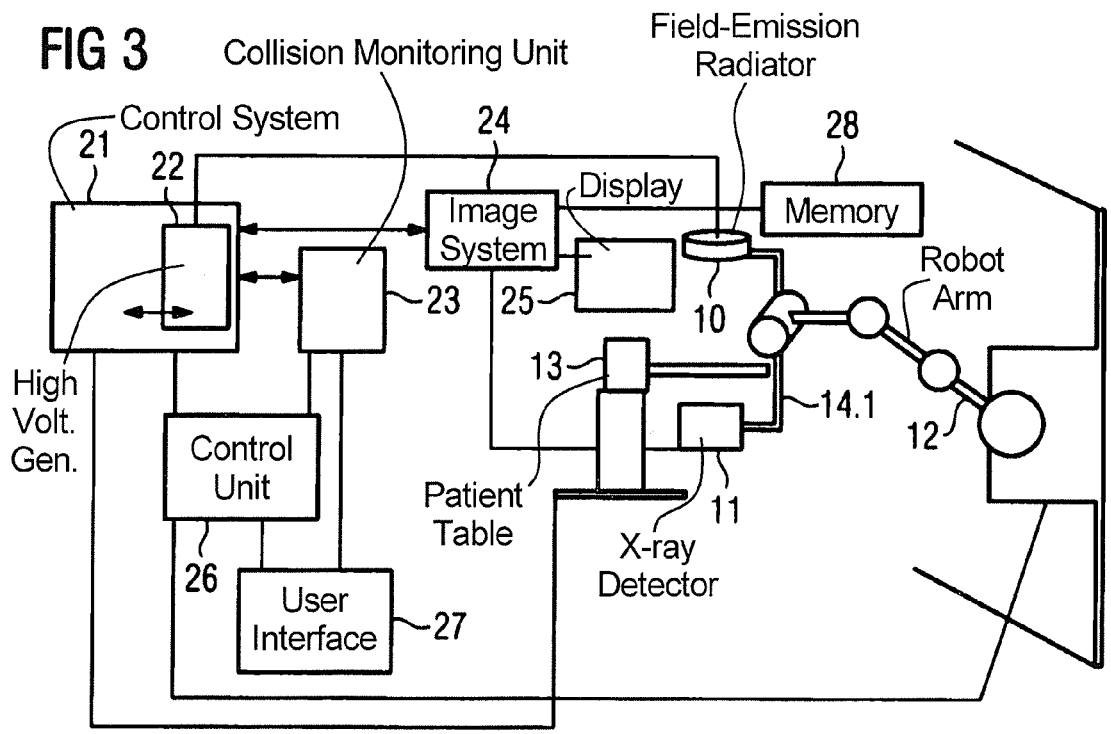

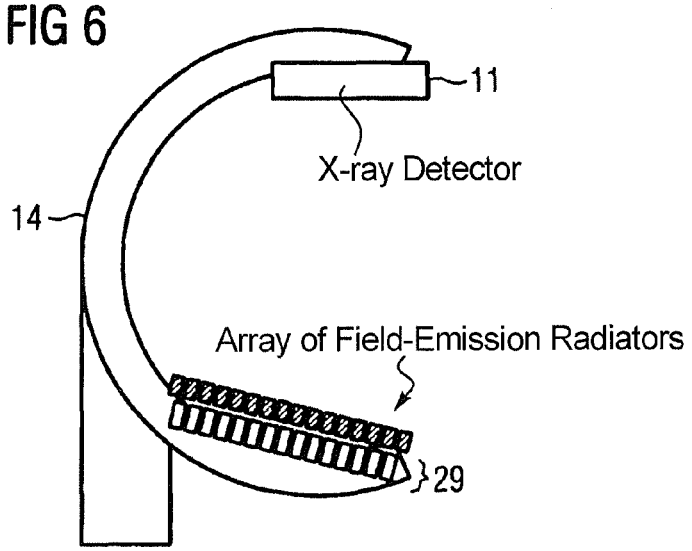
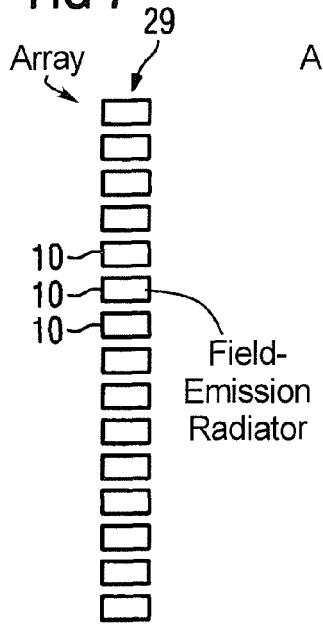
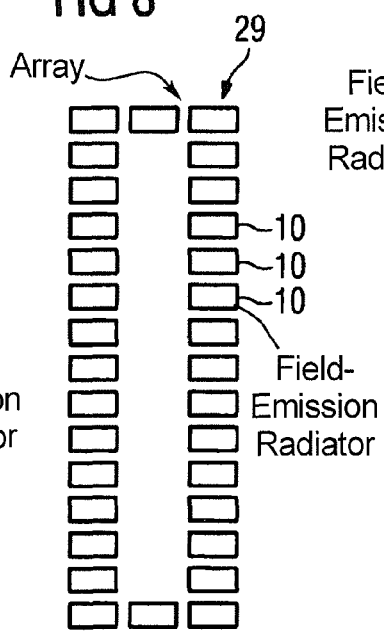
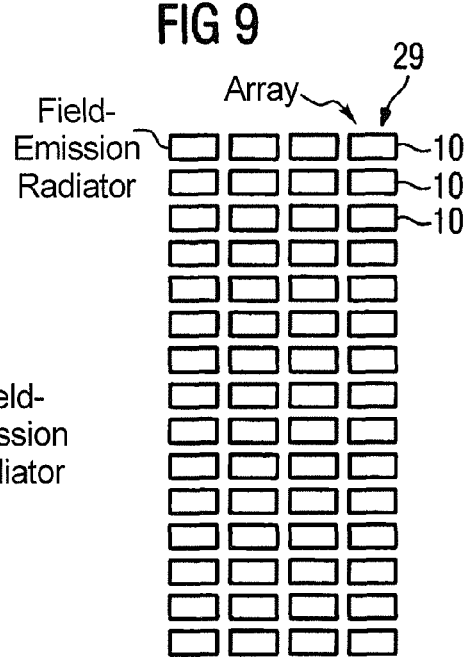

MEDICAL X-RAY ACQUISITION SYSTEM

BACKGROUND OF THE INVENTION

1. Field of the Invention

The invention concerns a medical x-ray acquisition system with an x-ray source and an x-ray detector

2. Description of the Prior Art

In known medical x-ray technology, vacuum tubes have been used for decades as x-ray sources in order to generate ionizing x-ray radiation. In such tubes, an electron beam is emitted from a metal filament cathode heated to above 1000° C. in an evacuated glass tube and is accelerated toward a metal anode (made of tungsten, for example), at which x-ray radiation is generated. Such a vacuum tube with a rotating anode is known from U.S. Pat. No. 4,326,144, for example. Among other things, known vacuum tubes have the disadvantages of a high weight (both due to the weight of the tube itself and due to an additional necessary water cooling), large dimensions, a low efficiency and a high heat generation.

SUMMARY OF THE INVENTION

An object of the present invention is to provide an x-ray acquisition system with an improved x-ray source, in particular an x-ray source suitable for medical applications.

The medical x-ray acquisition system according to the invention has an x-ray source and an x-ray detector, and the x-ray source has at least one field emission radiator with at least one field emission cathode. In a field emission cathode, electrons are emitted by the application of a sufficiently high electrical field. For example, field emission is achieved using a simple diode mode in which a bias voltage is applied between the anode and cathode of the radiator. Electrons are emitted by the cathode when the electrical field exceeds the threshold for the emission. A triode construction can also be provided in which a gate electrode is arranged near the cathode. Electrons are emitted in this embodiment by a bias voltage applied between the gate and the cathode. The emitted electrons are subsequently accelerated between the gate and the anode by a high voltage therebetween. Field emission cathodes allow a very high, well-controllable and easily focusable electron beam current. Overall, by the use of a field emission radiator the invention has the advantages of a low heat development of the x-ray source an a low weight, both due to the field emission radiator itself and due to the omission, or the reduction of a cooling system. Such a field emission radiator also exhibits a high degree of compactness in comparison to conventional x-ray radiators. The lifespan of field emission radiators is markedly higher than that of known x-ray radiators with thermal cathodes. In addition, in comparison to a thermal cathode a field emission cathode can be started quickly without heating. A higher spatial resolution can additionally be achieved by the electron flow that can be focused well. Overall, an x-ray source with a field emission radiator is also particularly suitable for new applications in which fast movements of the x-ray source or the entire acquisition system made up of x-ray source and x-ray detector are necessary.

According to one embodiment of the invention, the field emission cathode has a nanostructured material with carbon nanotubes (known as a CNT cathode; carbon nanotube). Such materials exhibit a particularly good emission characteristic, are also stable at high currents and can additionally be manufactured particularly small.

The x-ray source advantageously has a field emission radiator with a number of field emission cathodes. Alternatively, the x-ray source can have a number of field emission radiators. In this way a uniform radiation or radiation successively in very short intervals at different locations can be generated over a large area. A number of parallel beams can additionally be generated and radiated toward the x-ray detector so that particularly little scatter radiation and a high spatial resolution can be achieved.

According to a further embodiment of the invention, the field emission radiator is fashioned so as to be elliptical, circular or rectangular. In particular, the field emission radiator can exhibit a basic shape corresponding to the x-ray detector that is employed or its active surface. Alternatively, given a number of field emission radiators the field emission radiators are arranged in a linear, elliptical, circular or rectangular array.

According to further embodiments of the invention, the x-ray acquisition system is a fluoroscopy or radioscopy system, or an angiography or cardio-angiography system, or a projection x-ray system.

The x-ray source and the x-ray detector are advantageously held together by a C-arm or U-bracket. Such a C-arm or U-bracket can also be arranged on a multi-axis robot arm, in particular on an articulated arm robot with six rotation axes, in order to be able to be moved in arbitrary movement paths.

According to a further embodiment of the invention, the field emission radiators are arranged along a circle segment of the C-arm, for example over a specific angle range of 10°, 20° or 40°. In this way movements of the C-arm can be replaced or assisted by sequential operation of different field emission radiators. A method to acquire a number of projection images at different angle positions via sequential activation of the field emission radiators arranged along the C-arm can be advantageously implemented with such a medical x-ray acquisition system, and the projection images can subsequently be reconstructed into a volume image.

BRIEF DESCRIPTION OF THE DRAWINGS

FIG. 1 is a view of a field emission radiator with a field emission cathode.

FIG. 2 is a view of a field emission radiator with multiple field emission cathodes.

FIG. 3 is a view of a medical x-ray acquisition system with a U-bracket and a field emission radiator, and with additional system components.

FIG. 6 is a view of a C-arm with an array of field emission radiators arranged thereon.

FIG. 7 shows an example of a shape of an array of field emission radiators.

FIG. 8 shows an additional example of the shape of an array of field emission radiators.

FIG. 9 shows an additional example of the shape of an array of field emission radiators.

DESCRIPTION OF THE PREFERRED EMBODIMENTS

Figure 4:
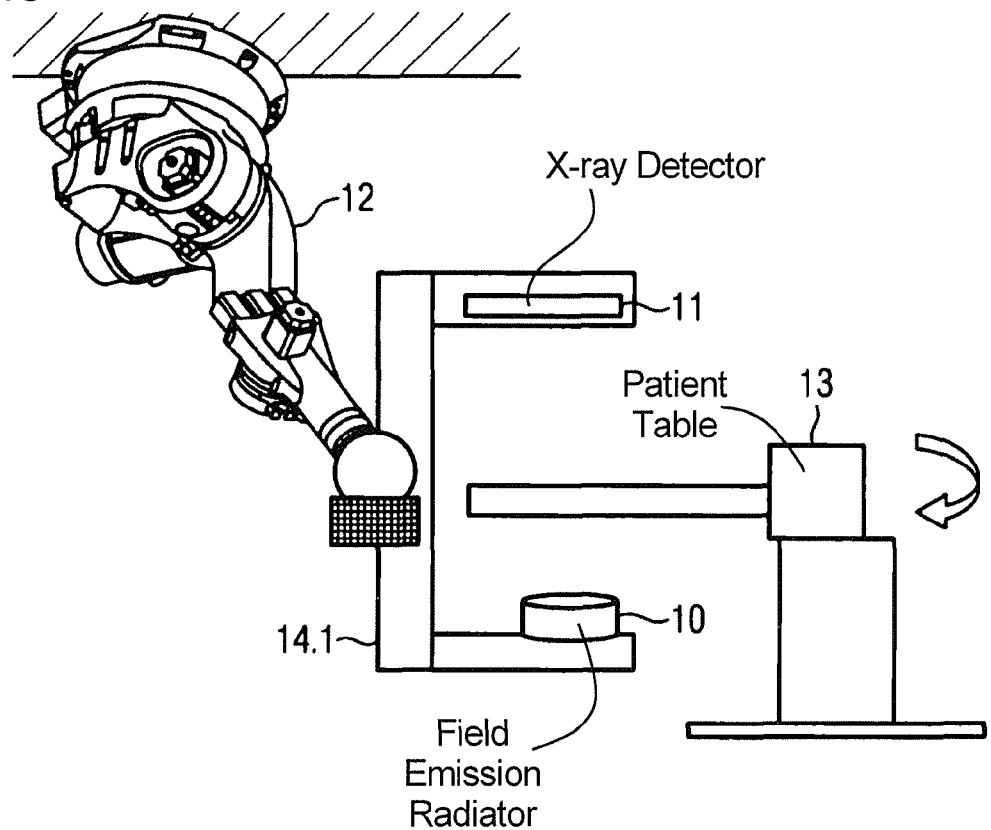
FIG. 4 is a view of an additional x-ray acquisition system with a U-bracket and a field emission radiator.

A field emission radiator 10 with a cathode 15 with a (single) electron-emitting element 18 and an anode 16 with a (single) focal spot 19 is shown in FIG. 1. Carbon, in particular in the form of nanotubes (CNT cathode) is thereby the material which is particularly well suited as a cathode in order to generate the high electron flow densities that are necessary. By applying an appropriate electrical field, the electron-emitting element 18 is induced (without heating) to emit an electron beam 17 which subsequently strikes the anode 16 or, respectively, the focal spot 19 and generates x-ray radiation there.

A further embodiment of a field emission radiator 10 is shown in FIG. 2, which field emission radiator possesses a cathode with a number of electron-emitting elements 18 that can all be activated individually. The elements 18 can be arranged in the manner of pixels. The anode 16 likewise is composed of a number of focal spots 19, with each focal spot 19 being associated with each electron-emitting element 18. The anode can be composed of copper, tungsten, molybdenum or an alloy of these metals, for example. Another gate electrode (not shown) can be arranged between the cathode and the anode in order to better control the electron emission from the cathode. The field emission radiator with a number of cathodes and anodes can be circular as shown in FIG. 2, for example, or be shaped as an ellipse or rectangle; the electron-emitting elements and focal spots can exhibit arbitrary arrangements, for example like a checkerboard or in circular paths.

A medical x-ray acquisition system with a U-bracket 14.1 and a field emission radiator 10 as well as an associated controller is shown in FIG. 3. A U-bracket 14.1 (or a C-arm) is arranged on a robot arm 12 (which, for example, is arranged on the wall or on the floor), which U-bracket 14.1 (or C-arm) in turn holds a field emission radiator 10 with one or more electron-emitting elements 18 as well as an x-ray detector 11. Such a design can be formed as a fluoroscopy/radioscopy system or angio/cardio-angiography system.

Moreover, in general in medical x-ray acquisition systems a control system 21 is provided to control the x-ray acquisition system; give the presence of a robot, a control unit 26 for the robot and a collision monitoring unit 23 are also provided. The control unit 26 for the robot and the collision monitoring unit 23 can also be integrated into the control system. A high voltage generator 22 is provided to supply the field emission radiator 10. To process and display acquired x-ray images or image series, an image system 24 and a display 25 are provided. A first user interface 27 is provided to input commands and or operation; an additional user interface 27 can optionally be provided for additional components. The image system 24 can have a pre-processor and a memory 28. Moreover, in general a patient bed 13 is provided. This can be attached to the floor and be capable of being displaced and/or tilted, for example.

The x-ray acquisition system can be formed by a fluoroscopy/radioscopy system or an angiography/cardio-angiography system or a projection x-ray system.

A radioscopy/fluoroscopy system is provided for the continuous acquisition of image series and is in particular used in gastrointestinal examinations. Radioscopy systems can be fashioned as below-table systems, above-table systems or universal systems and—because of the high radiation dose due to the continuous acquisition—frequently have the capability of being operated by remote control from a radiation-shielded room.

An example of an under-table system is shown in FIG. 4, in which a ceiling-mounted robot 12 holds a U-bracket 14.1 with a field emission radiator 10 and an x-ray detector 11. The x-ray detector can be permanently mounted or be insertable into a slot. For example, the x-ray detector can be a dynamic a-Si detector or an image intensifier with CCD camera; mobile flat panel detectors or film cartridges are also possible. The U-bracket 14.1 and the robot 12 as well as the radiation trigger and the patient table 13 can be operated via a remote control or even directly at the system, for example.

Figure 5:
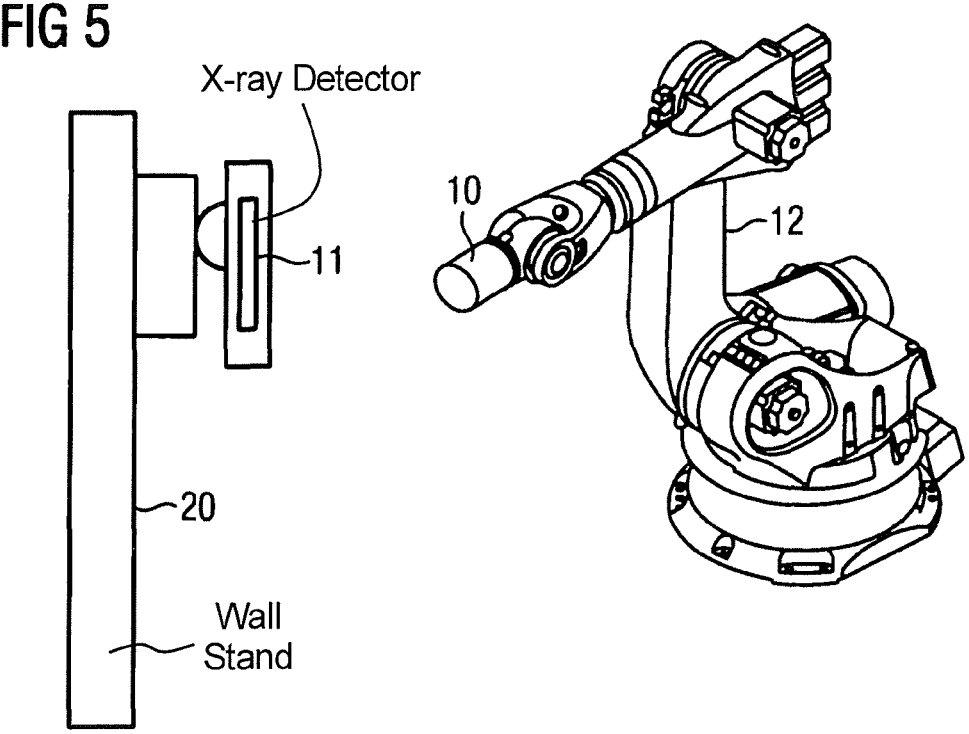
FIG. 5 is a view of an x-ray acquisition system with a field emission radiator arranged directly on an articulated arm robot.

A projection x-ray system is primarily used for simple projection exposures of thorax, pelvis, head and limbs and frequently possesses a simple design made up of x-ray source mounted either fixed or so as to be movable and x-ray detector mounted either fixed or so as to be movable. An example of a projection x-ray system with a field emission radiator 10 mounted on a robot 12 so as to be movable and a wall stand 20 with x-ray detector 11 mounted so as to be movable independent of the field emission radiator is shown in FIG. 5. Moreover, the field emission radiator 10 can be mounted on a floor stand, ceiling stand or other stand or on a telescoping arm and be arranged either fixed or movable by means of a motor.

An angiography/cardio-angiography system is used in particular for 3D exposures of heart and vessels and for a monitoring of minimally invasive procedures. For example, an angiography or cardio-angiography system according to the invention can possess a C-arm borne so as to be mobile on an articulated arm robot, with a field emission radiator and a flat panel detector, wherein the C-arm can be moved by the articulated arm robot into arbitrary translations and rotations and in particular is fashioned to acquire a plurality of projection images given a rotation around the examination subject, wherein the projection images can subsequently be reconstructed into a 3D image. A biplane system with two C-arms can also be provided, wherein at least one field emission radiator and one x-ray detector are respectively arranged at both C-arms. Alternatively, a single C-arm with two field emission radiators can also be provided, wherein the two field emission radiators are mounted with radial or axial separation and are aligned towards the same x-ray detector.

One, two or more field emission radiators can be provided in a medical x-ray acquisition system, wherein a single field emission radiator generally exhibits a higher power and a lower power per radiator can also be provided given a number of field emission radiators. As is shown in FIG. 6, multiple field emission radiators can be arranged as what is known as an array 29 along a circle segment of a C-arm 14, for example, wherein all field emission radiators are aligned toward the x-ray detector. Such an arrangement can be flat (as is shown in FIG. 6) or can also be fashioned directly adapted to the curvature of the C-arm. For example, an array 29 can extend over an angle range of the curvature of the C-arm, for example of 5° or 10° or 20° or 40°. Possible array shapes are shown in FIG. 7 through 9. FIG. 7 shows a linear arrangement of field emission radiators and FIG. 9 shows a checkerboard-like arrangement.

Mechanical movements of the C-arm can be replaced or assisted by sequential operation of different field emission radiators by means of the arrangement of an array 29 along a circle segment of the C-arm 14. Instead of a rotation of the C-arm in its circumferential direction around an examination subject, given a linear arrangement according to FIG. 7 (for example) the field emission radiators can be activated in sequence to emit radiation, and a series of projection exposures are thereby acquired at different angle positions. For example, a first field emission radiator arranged at the edge of the array is activated to emit radiation and a first projection image is acquired; a second field emission radiator arranged next to the first field emission radiator is subsequently activated and a second projection image is acquired. The series is continued until the opposite end of the array, for example, until a plurality of projection images has been acquired. These projection images can subsequently be reconstructed into a volume image and replace a mechanical rotation of the C-arm. Only individual field emission radiators from the array can also be activated if, for example, only two projection images at two different angulations are necessary. Given an arrangement according to FIG. 8 or FIG. 9, certain left/right movements of the x-ray focus can additionally be implemented without mechanical movement.

Angulations of more than 40° (for example 60°) can also be covered by means of an array (which covers an angle range of 40°, for example) if an activation of different field emission radiators is combined with mechanical displacement. In such a case only a mechanical panning of 20° is then necessary; the change from one angulation to a second angulation is achieved via combination of mechanical displacement and selection of a different field emission radiator. In the case of 3D acquisitions in which a fast panning over large angle ranges (of 200°, for example) is necessary, mechanical panning and electronic through-switching can likewise be combined in order to achieve a higher acquisition speed. In the case of an array that covers 40°, it must be rotated only by 160°, for example, which is possible in a shorter amount of time.

The invention can be summarized briefly as an improved medical x-ray acquisition system with an x-ray source and an x-ray detector wherein the x-ray source has at least one field emission radiator with at least one field emission cathode. In particular, the field emission cathode is composed of nanostructured material with carbon nanotubes.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical x-ray acquisition system comprising:
   an x-ray source;
   an x-ray detector;
   a C-arm to which said x-ray source and said x-ray detector are attached; and
   said x-ray source comprising a plurality of field emission radiators, each having at least one field emission cathode, said field emission radiators being arranged along a circle segment of the C-arm.

2. An x-ray acquisition system according to claim 1, wherein at least one field emission cathode respectively in at least one of said field emission radiators comprises a nanostructured material with carbon nanotubes.

3. An x-ray acquisition system according to claim 1, wherein at least one of said field emission radiators comprises a plurality of field emission cathodes.

4. An x-ray acquisition system according to claim 3, wherein said field emission radiators are respectively shaped as elliptical, circular or rectangular.

5. An x-ray acquisition system according to claim 1, the field emission radiators are arranged in a linear, elliptical, circular or rectangular array along said circle segment.

6. An x-ray acquisition system according to claim 1, wherein the x-ray source and the x-ray radiator form a fluoroscopy system.

7. An x-ray acquisition system according to claim 1, wherein the x-ray source and the x-ray radiator form an angiography system.

8. An x-ray acquisition system according to claim 1, wherein the x-ray source and the x-ray radiator form a projection x-ray system.

9. An x-ray acquisition system according to claim 1, wherein said C-arm is arranged on an articulated arm robot.

* * * * *